United States Patent
Learmonth et al.

(10) Patent No.: US 7,259,271 B2
(45) Date of Patent: Aug. 21, 2007

(54) PERIPHERALLY-SELECTIVE INHIBITORS OF DOPAMINE-β-HYDROXYLASE AND METHOD OF THEIR PREPARATION

(75) Inventors: David Alexander Learmonth, Alfena (PT); Patricio Manuel Viera Araújo Soares da Silva, Oporto (PT); Alexander Beliaev, Mindelo-Vila do Conde (PT)

(73) Assignee: Portela & C.A., S.A. (PT)

( * ) Notice: Subject to any disclaimer, the term of this patent is extended or adjusted under 35 U.S.C. 154(b) by 0 days.

(21) Appl. No.: 11/533,462

(22) Filed: Sep. 20, 2006

(65) Prior Publication Data

US 2007/0015730 A1 Jan. 18, 2007

Related U.S. Application Data

(62) Division of application No. 10/681,578, filed on Oct. 8, 2003.

(30) Foreign Application Priority Data

Oct. 11, 2002 (GB) ................... 0223719.6
Oct. 18, 2002 (GB) ................... 0224306.1

(51) Int. Cl.
C07F 7/04 (2006.01)
C07D 209/48 (2006.01)
C07C 211/00 (2006.01)

(52) U.S. Cl. ............... 556/418; 548/473; 549/23; 549/404; 564/305; 564/308; 564/428

(58) Field of Classification Search ............... 564/305, 564/308, 428; 549/23, 404; 556/418; 548/473
See application file for complete search history.

(56) References Cited

U.S. PATENT DOCUMENTS

| | | | |
|---|---|---|---|
| 5,210,162 A | | 5/1993 | Eck et al. |
| 5,288,748 A | * | 2/1994 | Wikstrom et al. .......... 514/411 |
| 5,438,150 A | | 8/1995 | Bansal et al. |
| 5,538,988 A | | 7/1996 | Martinez et al. |
| 5,719,280 A | | 2/1998 | Martinez et al. |

FOREIGN PATENT DOCUMENTS

| | | |
|---|---|---|
| EP | 0381451 A | 8/1990 |
| EP | 0222996 B1 | 5/1991 |
| EP | 0295983 B | 1/1993 |
| EP | 0611770 A | 8/1994 |
| EP | 0483465 B | 8/1995 |
| EP | 0466662 B | 10/1995 |
| EP | 0460169 B | 6/1996 |
| EP | 0730861 B | 9/1996 |
| EP | 1046646 A | 10/2000 |
| GB | 2290790 A | 1/1996 |
| WO | WO99/15494 | 4/1999 |
| WO | WO99/59988 | 11/1999 |
| WO | WO00/04901 | 2/2000 |
| WO | WO02/055112 | 7/2002 |
| WO | WO02/072559 | 9/2002 |

OTHER PUBLICATIONS

Malmberg et al, J. Med. Chem., vol. 39, pp. 4421-4429, 1996.*

* cited by examiner

*Primary Examiner*—Shailendra Kumar
(74) *Attorney, Agent, or Firm*—Rankin, Hill, Porter & Clark LLP (57) ABSTRACT

Compounds of formula I:

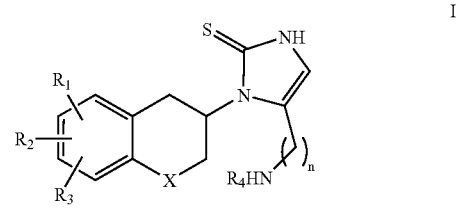

where $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl or alkylaryl group; X is $CH_2$, O or S, and n is 1, 2 or 3, with the proviso that if X is $CH_2$, n is not 1, and a method for their preparation. The compounds have potentially valuable pharmaceutical properties for the treatment of cardiovascular disorders such as hypertension and chronic heart failure.

12 Claims, 3 Drawing Sheets

PERIPHERALLY-SELECTIVE INHIBITORS OF DOPAMINE-β-HYDROXYLASE AND METHOD OF THEIR PREPARATION

CROSS-REFERENCE TO RELATED APPLICATIONS

This is a division of application Ser. No.10/681,578, filed Oct. 8, 2003 now U.S. Pat. No. 7,125,904.

BACKGROUND OF INVENTION

1. Field of Invention

This invention relates to peripherally-selective inhibitors of dopamine-β-hydroxylase and a method of their preparation.

2. Description of Related Art

In recent years, interest in the development of inhibitors of dopamine-β-hydroxylase (DβH) has centred on the hypothesis that inhibition of this enzyme may provide significant clinical improvements in patients suffering from cardiovascular disorders such as hypertension or chronic heart failure. The rationale for the use of DβH inhibitors is based on their capacity to inhibit the biosynthesis of noradrenaline, which is achieved via enzymatic hydroxylation of dopamine. Activation of neurohumoral systems, chiefly the sympathetic nervous system, is the principal clinical manifestation of congestive heart failure (Parmley, W. W., Clinical Cardiology, 18: 440-445, 1995). Congestive heart failure patients have elevated concentrations of plasma noradrenaline (Levine, T. B. et al., Am. J. Cardiol., 49:1659-1666, 1982), increased central sympathetic outflow (Leimbach, W. N. et al., Circulation, 73: 913-919, 1986) and augmented cardiorenal noradrenaline spillover (Hasking, G. J. et al., Circulation, 73:615-621, 1966). Prolonged and excessive exposure of myocardium to noradrenaline may lead to down-regulation of cardiac $\beta_1$-adrenoceptors, remodelling of the left ventricle, arrhytmias and necrosis, all of which can diminish the functional integrity of the heart. Congestive heart failure patients who have high plasma concentrations of noradrenaline also have the most unfavourable long-term prognosis (Cohn, J. N. et al., N. Engl. J. Med., 311:819-823, 1984). Of greater significance is the observation that plasma noradrenaline concentrations are already elevated in asymptomatic patients with no overt heart failure and can predict ensuing mortality and morbidity (Benedict, C. R. et al., Circulation, 94:690-697, 1996). This implies that the activated sympathetic drive is not merely a clinical marker of congestive heart failure, but may contribute to progressive worsening of the disease.

Inhibition of sympathetic nerve function with adrenoceptor antagonists appeared a promising approach, however a significant proportion of patients do not tolerate the immediate haemodynamic deterioration that accompanies β-blocker treatment (Pfeffer, M. A. et al., N. Engl. J. Med., 334:1396-7, 1996). An alternative strategy for directly modulating sympathetic nerve function is to reduce the biosynthesis of noradrenaline via inhibition of DβH, the enzyme responsible for conversion of dopamine to noradrenaline in sympathetic nerves. This approach has several merits including gradual modulation as opposed to abrupt inhibition of the sympathetic system, and causing increased release of dopamine, which can improve renal function such as renal vasodilation, diuresis and natriuresis. Therefore inhibitors of DβH may provide significant advantages over conventional β-blockers.

Several inhibitors of DβH have been thus far reported in the literature. Early first and second generation examples such as disulfiram (Goldstein, M. et al., Life Sci., 3:763, 1964) and diethyldithiocarbamate (Lippmann, W. et al., Biochem. Pharmacol., 18: 2507, 1969) or fusaric acid (Hidaka, H. Nature, 231, 1971) and aromatic or alkyl thioureas (Johnson, G. A. et al, J. Pharmacol. Exp. Ther., 171: 80, 1970) were found to be of low potency, exhibited poor selectivity for DβH and caused toxic side effects. The third generation of DβH inhibitors however, were found to have much greater potency, such as for example, nepicastat (RS-25560-197, $IC_{50}$ 9 nM) (Stanley, W. C., et al., Br. J Pharmacol., 121: 1803-1809, 1997), which was developed to early clinical trials. Although devoid of some of the problems associated with first and second generation DβH inhibitors, a very important discovery was that nepicastat was found to cross the blood brain barrier (BBB), thereby able to cause central as well as peripheral effects, a situation which could lead to undesired and potentially serious CNS side-effects of the drug. Therefore there yet remains an unfulfilled clinical requirement for a potent, non-toxic and peripherally selective inhibitor of DβH, which could be used for treatment of certain cardiovascular disorders. A DβH inhibitor with similar or even greater potency than nepicastat, but devoid of CNS effects (inability to cross the BBB) would provide a significant improvement over all DβH inhibitor compounds thus far described in the prior art.

BRIEF SUMMARY OF THE INVENTION

We have surprisingly found that incorporation of certain heteroatoms to the carbocyclic ring and/or elongation of the amino alkyl side-chain of the nepicastat core-structure gives rise to a series of compounds possessing significant and pronounced effects of potential usefulness for DβH inhibition. Many of these compounds are endowed with greater potency and significantly reduced brain access, giving rise to potent and peripherally selective DβH inhibitors. Thus, the invention relates to compounds of general formula I;

where $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl or alkylaryl group; X signifies $CH_2$, oxygen atom or sulphur atom; n is 1, 2 or 3, with the proviso that when n is 1, X is not $CH_2$; and the individual (R)- and (S)-enantiomers or mixtures of enantiomers; and the pharmaceutically acceptable salts thereof.

DETAILED DESCRIPTION OF THE INVENTION

The invention relates to compounds of general formula I;

where $R_1$, $R_2$ and $R_3$ are the same or different and signify hydrogens, halogens, alkyl, alkylaryl, alkyloxy, hydroxy, nitro, amino, alkylcarbonylamino, alkylamino or dialkylamino group; $R_4$ signifies hydrogen, alkyl or alkylaryl group; X signifies $CH_2$, oxygen atom or sulphur atom; n is 1, 2 or 3, with the proviso that when n is 1, X is not $CH_2$; and the individual (R)- and (S)-enantiomers or mixtures of enantiomers; and the pharmaceutically acceptable salts thereof.

Unless stated otherwise, in this specification the term alkyl (whether used on its own or used in combination with other moieties) means hydrocarbon chains, straight or branched, containing from one to six carbon atoms, optionally substituted by aryl, alkoxy, halogen, alkoxycarbonyl or hydroxycarbonyl groups; the term aryl (whether used on its own or used in combination with other moieties) means a phenyl or naphthyl group, optionally substituted by alkyloxy, halogen or nitro group; and the term halogen means fluorine, chlorine, bromine or iodine.

Another aspect of the present invention is a process for the preparation of compounds of formula I. Some compounds according to formula II where X signifies methylene ($CH_2$), oxygen or sulphur are known (Martinez, G. R. et al., U.S. Pat. No. 5,538,988, Jul. 23, 1996; Eriksson, M., PCT Int. Appl. WO 9959988A1, 25 Nov. 1999; Napoletano, M., PCT Int. Appl. WO 9608489A1, 21 Mar. 1996; Sarda, N. et al., Tetrahedron Lett., 17:271-272, 1976; Neirabeyeh, M. Al et al., Eur. J. Med. Chem., 26:497-504, 1991) in the literature and others can be prepared by those skilled in the art. Compounds according to formula II are chiral, and formula II is therefore to be taken to represent both optically pure individual (R)- and (S)-enantiomers or mixtures of enantiomers;

Compounds of formula I are prepared by reacting a compound of formula II where X is $CH_2$, oxygen or sulphur; $R_1$, $R_2$ and $R_3$ are the same or different and signify hydrogens, halogens, alkyl, alkylaryl, alkyloxy, hydroxy, nitro, alkylcarbonylamino, alkylamino or dialkylamino group with a compound of formula III:

where n signifies 1, 2 or 3; when n is 1 or 2, $R_4$ signifies hydrogen, alkyl or alkylaryl group; $R_5$ signifies a hydroxyl protecting group and $R_6$ signifies an amino protecting group; when n signifies 3, $R_5$ is defined as above but $R_4$ and $R_6$ taken together represent a phthalimido group; and with a water soluble thiocyanate salt in an inert organic solvent and in the presence of an organic acid, wherein the water soluble thiocyanate salt is an alkali metal thiocyanate salt or a tetraalkylammonium thiocyanate salt.

Suitable alkali metal thiocyanate salts include sodium, lithium and cesium thiocyanates, but potassium thiocyanate is preferred.

The compound of formula III where n is 1 is known (Wolf, E. et al., Can. J. Chem., 75:942-948, 1997) and compounds of formula III where n is 2 or 3 are new compounds that can be prepared by those skilled in the art (see examples). The preferred hydroxyl protecting groups ($R_5$) include organosilyl compounds such as chosen from trialkysilyl, triphenylsilyl, phenyldialkylsilyl or alkyldiphenylsilyl group. The tert-butyldimethylsilyl (TBDMS) group is especially preferred. The preferred amino protecting groups ($R_6$) include carbamates such alkyl carbamates, in particular the t-butyl carbamate (Boc) group, and alkylaryl carbamates. The reaction may be run with a small excess of the compound of formula III and potassium thiocyanate (preferably 1.1-1.3 equivalents).

The invention also provides compounds of formula II, where at least one of $R_1$, $R_2$ and $R_3$ is fluorine.

The reaction can be run in a substantially inert solvent (preferably ethyl acetate) and at different temperatures (preferably at the solvent reflux temperature). Preferred organic acids include acetic acid. When compounds of formula III where n signifies 1 are used, the intermediate of formula IV is then treated with a mineral acid in a suitable solvent to remove the Boc amino protecting group and provide the compounds of formula I (scheme 1). Preferred mineral acids include hydrochloric acid and preferred solvents include ethyl acetate.

When compounds of formula III where n signifies 2 are used and $R_4$ signifies hydrogen, the mixture of intermediate products of formula V and VI is reacted with hydrochloric acid in ethyl acetate to afford the corresponding single compounds of formula I (scheme 2); where $R_4$ signifies alkyl (including alkyl substituted by aryl), the single intermediate product of formula V is reacted with hydrochloric acid in ethyl acetate to afford the compounds of formula I.

When compounds of formula III where n is 3 are used, the intermediate of formula VII is then treated with sodium borohydride in a suitable solvent system followed by acetic acid to remove the pthalimido amino protecting group as described in the literature (Osby et al., Tetrahedron Lett., 1984, 25(20), 2093-2096) to give the compounds of formula I (scheme 3). The compounds of formula I are obtained with good purity, but if preferred can be recrystallised from a suitable solvent.

SCHEME 1

SCHEME 2

For the preparation of pharmaceutical compositions of compounds of formula I, inert pharmaceutically acceptable carriers are admixed with the active compounds. The pharmaceutically acceptable carriers may be either solid or liquid. Solid form preparations include powders, tablets, dispersible granules and capsules. A solid carrier can be one or more substances which may also act as diluents, flavouring agents, solubilizers, lubricants, suspending agents, binders or tablet disintegrating agents; it may also be an encapsulating material.

Preferably the pharmaceutical preparation is in unit dosage form, e.g. packaged preparation, the package containing discrete quantities of preparation such as packeted tablets, capsules and powders in vials or ampoules.

The dosages may be varied depending on the requirement of the patient, the severity of the disease and the particular compound being employed. For convenience, the total daily dosage may be divided and administered in portions throughout the day. It is expected that once or twice per day administration will be most suitable. Determination of the proper dosage for a particular situation is within the skill of those in the medical art.

MATERIALS AND METHODS IN VITRO STUDIES

DβH activity was evaluated by the ability to β-hydroxylate dopamine to noradrenaline as previously described (Kojima, K., Parvez, S. and Nagatsu T. 1993. Analysis of enzymes in catecholamine biosynthesis. In Methods in Neurotransmitter and Neuropeptide Research, pp. 349-380: Elsiever Science Publishers). SK-N-SH cells (ATCC HTB-11), a human neuroblastoma derived cell line, were used as a source of human DβH. SK-N-SH cells cultured in 24 well plates were preincubated for 20 min in a reaction medium containing 200 mM sodium acetate, 30 mM N-ethylmaleimide, 5 µM copper sulphate, 0.5 mg/ml catalase aqueous solution, 1 mM pargyline, 10 mM sodium fumarate and 20 mM ascorbic acid. Thereafter, cells were incubated for further 45 min in the reaction medium with added increasing concentrations of dopamine (0.5 to 100 mM). During pre-incubation and incubation, the cells were continuously shaken and maintained at 37° C. The reaction was terminated by the addition of 0.2 M perchloric acid. The acidified samples were stored at 4° C. before injection into the high pressure liquid chromatograph for the assay of noradrenaline. In experiments conducted with the aim of studying the effects of new DβH inhibitors on enzyme activity, test compounds (0.3 to 10,000 nM) of interest were added to the preincubation and incubation solutions; the incubation was performed in the presence of a concentration (50 mM) of dopamine 2.5 times the corresponding $K_m$ value as determined in saturation experiments.

In Vivo Studies

Male NMRI mice or Wistar rats were obtained from Harlan-lnterfauna (Spain) and were kept 10 and 5 per cage respectively, under controlled environmental conditions (12 h light/dark cycle and room temperature 22±1° C.). Food and tap water were allowed ad libitum and experimentation was performed during daylight hours.

At time =0 h, animals were administered with either test compounds at a given dose or vehicle (water) delivered orally via gavage. At 2, 6, 9, 12, 18 and 24 h post dose, the animals were sacrificed by decapitation and heart (left atrium and left ventricle) and brain (frontal and parietal cortex) were isolated, weighed and stored in a volume of 0.2 M perchloric acid for 12 h at 4° C. in the dark. Post incubation, the resulting supernatants were collected by centrifuge filtration of incubates (0.2 µM/10 min/~5000 rpm, 4° C.). Supernatants were stored frozen at −80° C. until analysis. Quantification of dopamine and noradrenaline in supernatants was performed by high pressure liquid chromatography with electrochemical detection.

Results In Vitro Studies

Incubation of SK-N-SH cells in the presence of increasing concentrations of dopamine resulted in a concentration-dependent formation of noradrenaline, yielding $K_m$ (in µM) and $V_{max}$ (in nmol mg protein$^{-1}$ h$^{-1}$) values of 20.6±1.6 and 153.8±4.4, respectively. From these kinetic parameters, a concentration of dopamine approaching saturation (50 mM) was chosen for use in inhibition studies. As listed in Table 1 compounds 2,3,4,5,6,7,8,10,12,16,19,24,26,28 and 29 were found to markedly inhibit DβH activity. Compounds 2, 3, 4 and nepicastat 1 (the reference compound) produced a concentration-dependent decrease in the β-hydroxylation of dopamine with $IC_{50}$ values in the low nM range against human DβH activity (see Table 2). Compound 4 was chosen for further in vivo studies, being the compound most closely related to nepicastat 1 in order to provide conclusive evidence that the structural modifications made to the molecule as part of the present invention are responsible for the surprisingly markedly improved biological properties observed.

TABLE 1*

| No. | Mean ± SEM |
|---|---|
| 1 | 0.0 ± 0.3 |
| 2 | 1.6 ± 0.3 |
| 3 | 4.1 ± 0.6 |
| 4 | 3.3 ± 0.3 |
| 5 | 8.1 ± 0.3 |
| 6 | 6.9 ± 0.6 |
| 7 | 8.0 ± 0.1 |
| 8 | 9.4 ± 0.7 |
| 9 | 50.2 ± 1.9 |
| 10 | 8.2 ± 0.7 |
| 11 | 36.7 ± 4.4 |
| 12 | 3.0 ± 0.5 |
| 13 | 94.0 ± 3.1 |
| 14 | 77.9 ± 2.2 |
| 15 | 86.1 ± 2.7 |
| 16 | 0.0 ± 0.6 |
| 17 | 53.2 ± 3.9 |
| 18 | 94.8 ± 1.2 |
| 19 | 6.9 ± 0.5 |
| 20 | 16.8 ± 4.8 |
| 21 | 124.8 ± 6.5 |
| 22 | 17.8 ± 2.1 |
| 23 | 54.5 ± 9.9 |
| 24 | 0.0 ± 1.9 |
| 25 | 66.0 ± 4.5 |
| 26 | 4.5 ± 1.9 |
| 27 | 15.5 ± 5.8 |
| 28 | 2.6 ± 1.6 |
| 29 | 2.2 ± 2.5 |
| 30 | 99.4 ± 2.8 |
| 31 | 27.3 ± 0.4 |

*Effect of selected compounds (5 µM) on DβH activity in SK-N-SH cells. Values are quoted as % of control

TABLE 2*

| Compound | $IC_{50}$ (in nM) |
|---|---|
| 2 | 60 (14, 250) |
| 3 | 91 (56, 147) |
| 4 | 105 (69, 161) |
| Nepicastat 1 | 36 (28, 46) |

*$IC_{50}$ values (in nM) for inhibition of DβH in SK-N-SH cells.

In Vivo Studies Mouse

Figure 1:
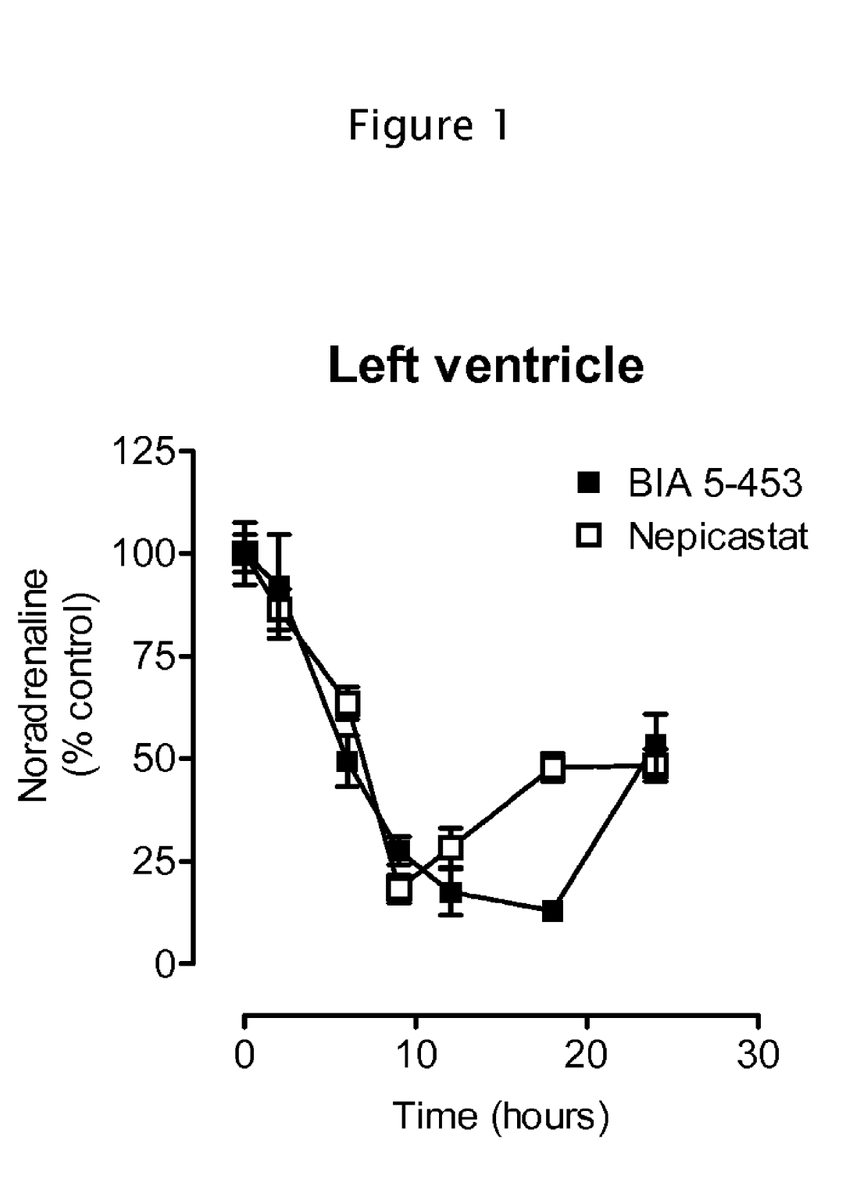
FIG. 1 is a graph showing a time-dependent decrease of noradrenaline levels in the left ventricle of mice treated orally with a compound according to the invention as compared to a reference standard.

The time course experiments for compound 4 and nepicastat (1) in the heart at 100 mg/kg suggests that both compounds are long acting. Time of maximum effect ($T_{max}$) for noradrenaline tissue reduction by both 4 and 1 appears to be at 9 h post-dose (FIG. 1). Thereafter, noradrenaline tissue levels recover, reaching 50% recovery of initial tissue levels at 24 h.

Figure 2:
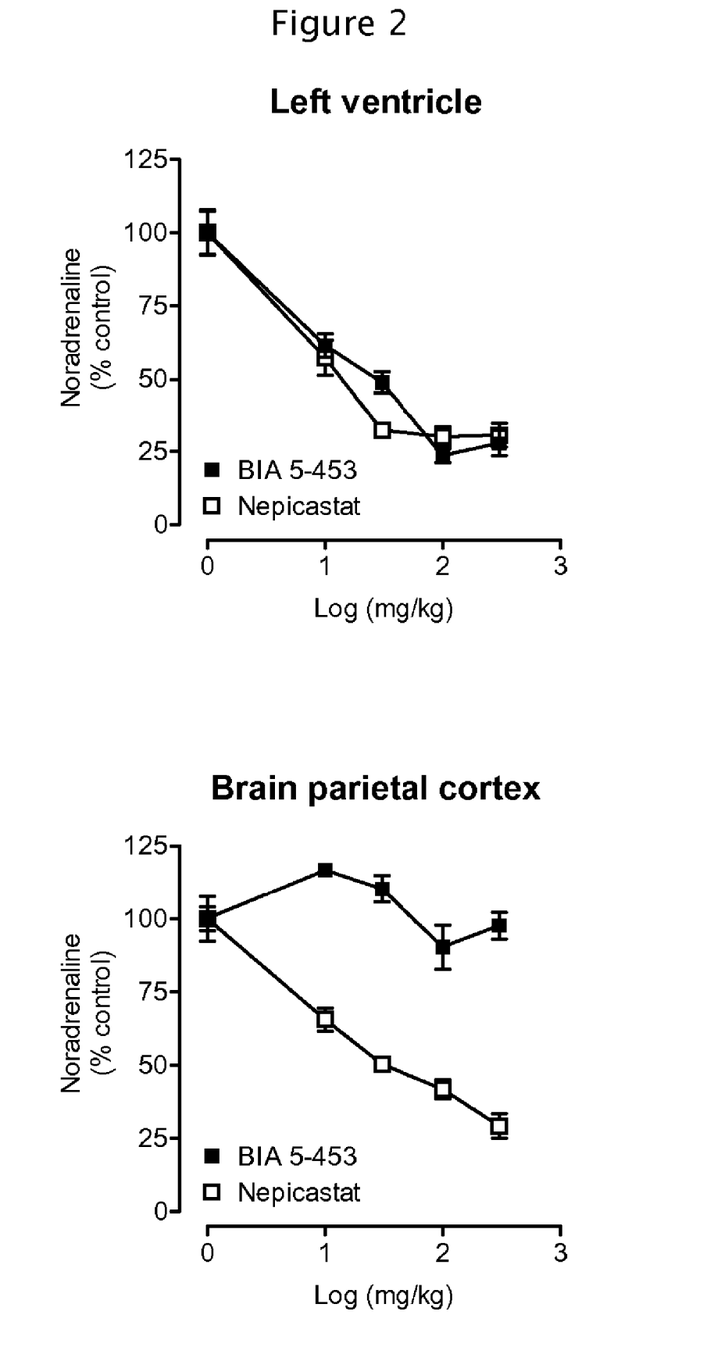
FIG. 2 is two graphs showing noradrenaline levels in the left ventricle and brain parietal cortex of mice after oral administration of a compound according to the invention as compared to a reference standard.

At $T_{max}$ (9 h after administration), both 4 and 1 reduced noradrenaline levels in a dose-dependent manner in left ventricle. For both 4 and 1, the maximal inhibitory effect was attained at a dose of 100 mg/kg. In contrast to that found in the heart, 4 failed to affect noradrenaline tissue levels in the brain parietal cortex, whereas 1 produced a dose-dependent decrease in noradrenaline levels in this area of the brain (FIG. 2).

Rat

Figure 3:
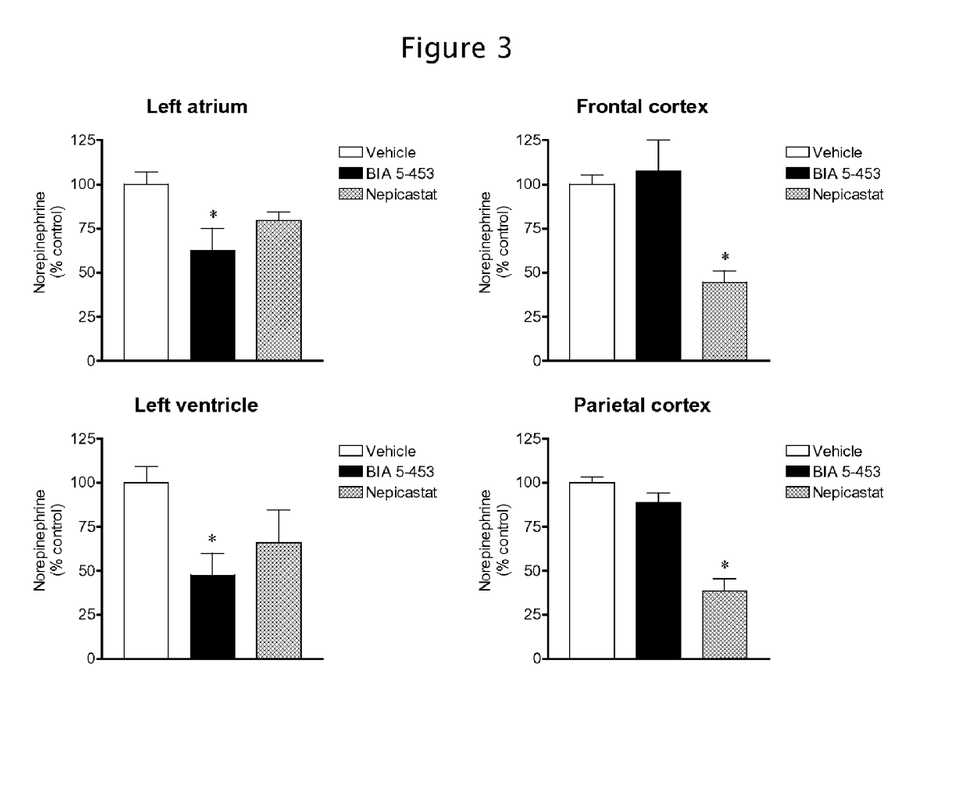
FIG. 3 is four graphs showing noradrenaline levels in the heart and brain of a rat after oral administration of a compound according to the invention as compared to a reference standard.

As shown in the mouse, the effects of both 4 and 1 upon noradrenaline were dependent on the dose administered and reached its maximum at 9 h (data not shown). However, as depicted in FIG. 3, the inhibitory effects of 4 (100 mg/kg) upon noradrenaline levels in both the left atrium and the left ventricle were more pronounced than those elicited by 1 (100 mg/kg). Again, as observed in the mouse, 4 failed to affect noradrenaline tissue levels in the brain parietal cortex and the brain frontal cortex, whereas 1 produced a marked decrease in noradrenaline levels in these brain areas.

It is concluded that 4, in stark contrast to nepicastat 1, exerts its inhibitory effects upon DβH exclusively in the periphery, being devoid of inhibitory effects in the brain.

Reference is now made to the accompanying drawings, in which:

FIG. 1 is a graph showing the time-dependent decrease of noradrenaline levels in the left ventricle of mice treated orally with 100 mg/kg of 4 or nepicastat 1. Symbols are means of 5 determinations per group; vertical lines indicate S.E.M.

FIG. 2 is two graphs showing noradrenaline levels in the mouse left ventricle and brain parietal cortex 9 h after oral administration of 4 or nepicastat 1. Symbols are means of 5 determinations per group; vertical lines indicate S.E.M.

FIG. 3 is four graphs showing noradrenaline levels in the rat heart (left atrium and left ventricle) and brain (frontal and parietal cortex) 9 h after the oral administration of 4 or nepicastat 1. Columns are means of 5 determinations per group; vertical lines indicated S.E.M.

Conclusion

Some compounds of general formula I are very potent dopamine-β-hydroxylase inhibitors and have potentially valuable pharmaceutical properties in the treatment of some cardiovascular disorders, where a reduction in the enzymatic hydroxylation of dopamine to noradrenaline may be of therapeutic benefit, such as hypertension and chronic heart failure. The possibility to use a long-acting DβH inhibitor with limited access to the brain (CNS), such as compound 4 opens new perspectives in the treatment of hypertension and chronic heart failure by improving potency and selectivity of DβH inhibition in the periphery.

The invention disclosed herein is exemplified by the following examples of preparation, which should not be construed to limit the scope of the disclosure. Alternative pathways and analogous structures may be apparent to those skilled in the art.

EXAMPLE 1

(R)-5-aminomethyl-1-(6,8-difluorochroman-3-yl)-1,3-dihydroimidazole-2-thione hydrochloride (compound 3, Table 1)

A stirred mixture of (R)-6,8-difluorochroman-3-ylamine hydrochloride (0.22 g, 1.0 mmol), [3-(tert-butyldimethylsilanyloxy)-2-oxopropyl]carbamic acid tert-butyl ester (0.33 g, 1.1 mmol), potassium thiocyanate (0.11 g, 1.1 mmol) and acetic acid (0.3 mL, 5.0 mmol) in ethyl acetate (3 mL) was refluxed for 2 hours, cooled to room temperature, then washed by sodium bicarbonate solution, dried over anhydrous magnesium sulphate and evaporated in vacuo. The residue was purified by the column chromatography over silica gel using ethyl acetate—petroleum ether mixture as eluent. The resulting oil (0.23 g) was dissolved in ethyl acetate (2 ml), whereupon 2M HCl solution in ethyl acetate was added (2 mL, 4 mmol) and the mixture was stirred for 2 hours at room temperature. The precipitate was removed by filtration and washed with ethyl acetate to give crystals of m.p. 192° C. (decomp.).

EXAMPLES 2-3

By the application of the above described technique and related procedures known to those skilled in the art and using the appropriate chroman-3-ylamines hydrochlorides, the following compounds were prepared:

(R)-5-aminomethyl-1-chroman-3-yl-1,3-dihydroimidazole-2-thione hydrochloride (compound 24, table 1)

(R)-5-aminomethyl-1-(6-hydroxychroman-3-yl)-1,3-dihydroimidazole-2-thione hydrochloride (compound 22, table 1)

EXAMPLE 4

(R,S)-5-aminomethyl-1-(6-hydroxythiochroman-3-yl)-1,3-dihydroimidazole-2-thione hydrochloride A stirred mixture of 6-hydroxythiochroman-3-ylamine hydrochloride (0.22 g, 1.0 mmol), [3-(tert-butyldimethylsilanyloxy)-2-oxopropyl]carbamic acid tert-butyl ester (0.33 g, 1.1 mmol), potassium thiocyanate (0.11 g, 1.1 mmol) and acetic acid (0.3 mL, 5.0 mmol) in ethyl acetate (3 mL) was refluxed for 2 hours, then cooled to room temperature, and washed by sodium bicarbonate solution, dried over anhydrous magnesium sulphate and evaporated in vacuo. The residue was purified by column chromatography on silica using ethyl acetate—petroleum ether mixture as eluent. The resulting oil (0.25 g) was dissolved in ethyl acetate (2 ml), whereupon 2M HCl solution in ethyl acetate was added (2 mL, 4 mmol) and the mixture was stirred for 2 hours at room temperature. The precipitate was removed by filtration and washed with ethyl acetate to give crystals, which decomposed without melting.

EXAMPLE 5

(3,4-Dihydroxybutyl)carbamic acid tert-butyl ester

To a stirred solution of 4-amino-1,2-propanediol (2.10 g, 20 mmol) in ethanol (50 mL) at room temperature was added di-tert-butyldicarbonate (4.80 g, 22 mmol) in one portion. The resulting mixture was stirred at room temperature for two hours, then evaporated in vacuo and purified by column chromatography on silica using ethyl acetate—petroleum ether mixture as eluent to afford colourless oil.

EXAMPLES 6-7

By the application of the above described technique and related procedures known to those skilled in the art and using the appropriate N-substituted 4-amino-1,2-propanediols, the following compounds were prepared:

(3,4-Dihydroxybutyl)methylcarbamic acid tert-butyl ester (3,4-Dihydroxybutyl)benzylcarbamic acid tert-butyl ester

EXAMPLE 8

[4-(tert-butyldimethylsilanyloxy)-3-hydroxybutyl] carbamic acid tert-butyl ester To a stirred solution of (3,4-dihydroxybutyl)carbamic acid tert-butyl ester (2.60 g, 12.7 mmol), triethylamine (2.03 mL, 14.50 mmol) and 4-(dimethylamino)pyridine (0.05 g, 0.4 mmol) in anhydrous dichloromethane (40 mL) at room temperature was added tert-butyldimethylchlorosilane (2.0 g, 13.17 mmol) in one portion. The resulting mixture was stirred at room temperature for 18 hours, washed with water, brine and dried over anhydrous magnesium sulfate. Filtration and concentration in vacuo gave an oil which was purified by column chromatography on silica using ethyl acetate—petroleum ether mixture as eluent to afford a colourless oil.

EXAMPLES 9-10

By the application of the above described technique and related procedures known to those skilled in the art and using compounds from examples 6 and 7, the following compounds were prepared:
[4-(tert-butyldimethylsilanyloxy)-3-hydroxybutyl]methylcarbamic acid tert-butyl ester
[4-(tert-butyldimethylsilanyloxy)-3-hydroxybutyl]benzylcarbamic acid tert-butyl ester

EXAMPLE 11

[4-(tert-butyldimethylsilanyloxy)-3-oxobutyl]carbamic acid tert-butyl ester

To a solution of Dess-Martin periodinane (5.0 g, 11.8 mmol) in anhydrous dichloromethane (35 mL) at room temperature was added a solution of [4-(tert-butyldimethylsilanyloxy)-3-hydroxybutyl]carbamic acid tert-butyl ester (3.77 g, 11.8 mmol) in anhydrous dichloromethane. The resulting mixture was stirred at room temperature for one hour, evaporated in vacuo to one third of the initial volume and applied to a column packed with silica. Elution with ethyl acetate—petroleum ether solvent mixture afforded a colorless oil.

EXAMPLES 12-13

By the application of the above described technique and related procedures known to those skilled in the art and using compounds from examples 9 and 10, the following compounds were prepared:
[4-(tert-butyldimethylsilanyloxy)-3-oxobutyl]methylcarbamic acid tert-butyl ester
[4-(tert-butyldimethylsilanyloxy)-3-oxobutyl]benzylcarbamic acid tert-butyl ester.

EXAMPLE 14

(S)-5-(2-aminoethyl)-1-(5,7-difluoro-1,2,3,4-tetrahydronaphthalen-2-yl)-1,3-dihydroimidazole-2-thione hydrochloride, compound 2, table 1)

A stirred mixture of (S)-5,7-difluoro-1,2,3,4-tetrahydronaphthalen-2-yl amine hydrochloride (0.17 g, 0.79 mmol), [4-(tert-butyldimethylsilanyloxy)-3-oxobutyl]carbamic acid tert-butyl ester (0.28 g, 0.87 mmol), potassium thiocyanate (0.085 g, 0.85 mmol), water (0.014 mL, 0.80 mmol) and acetic acid (0.2 mL, 3.3 mmol) in ethyl acetate (2 mL) was refluxed for 7 hours, cooled to the room temperature, washed by sodium bicarbonate solution and dried over anhydrous magnesium sulphate and evaporated in vacuo. The residue was purified by column chromatography on silica using ethyl acetate—petroleum ether mixture as eluent. The resulting oil (0.24 g) was dissolved in ethyl acetate (2 ml), 2M HCl solution in ethyl acetate was added (2 mL, 4 mmol) and the mixture was stirred for 2 hours at room temperature. The precipitate was removed by filtration and washed with ethyl acetate to give crystals, which decomposed without melting.

EXAMPLE 15

By the application of the above described technique and related procedures known to those skilled in the art and using the appropriate 1,2,3,4-tetrahydronaphthalen-2-ylamines hydrochlorides, the following compounds were prepared:
(S)-5-(2-aminoethyl)-1-(1,2,3,4-tetrahydronaphthalen-2-yl)-1,3-dihydroimidazole-2-thione hydrochloride (compound 20, table 1)

EXAMPLE 16

(R)-5-(2-aminoethyl)-1-(6,8-difluorochroman-3-yl)-1,3-dihydroimidazole-2-thione hydrochloride (compound 4, table 1)

A stirred mixture of (R)-6,8-difluorochroman-3-ylamine hydrochloride (1.68 g, 7.58 mmol), [4-(tert-butyldimethylsilanyloxy)-3-oxobutyl]carbamic acid tert-butyl ester (3.13 g, 9.85 mmol), potassium thiocyanate (0.96 g, 9.85 mmol), water (0.18 mL, 10 mmol) and acetic acid (3.0 mL, 50 mmol) in ethyl acetate (30 mL) was refluxed for 7 hours, cooled to room temperature, washed by sodium bicarbonate solution, dried over anhydrous magnesium sulphate and evaporated in vacuo. The residue was purified by column chromatography on silica using ethyl acetate—petroleum ether mixture as eluent. The resulting oil (2.15 g) was dissolved in ethyl acetate (20 ml), 2M HCl solution in ethyl acetate was added (20 mL, 40 mmol) and the mixture was stirred for 2 hours at room temperature. The precipitate was removed by filtration and washed with ethyl acetate to give crystals, which decomposed without melting.

EXAMPLES 17-37

By the application of the above described technique and related procedures known to those skilled in the art and using the appropriate chroman-3-ylamine hydrochlorides and [4-(tert-butyldimethylsilanyloxy)-3-oxobutyl]carbamic acid tert-butyl esters, the compounds listed in Table 3 were prepared:

TABLE 3

| Ex. | Compound | Ref to Table 1 |
|---|---|---|
| 17 | (R)-5-(2-aminoethyl)-1-chroman-3-yl-1,3-dihydroimidazole-2-thione hydrochloride | Compound 12 |
| 18 | (R)-5-(2-aminoethyl)-1-(6-hydroxychroman-3-yl)-1,3-dihydroimidazole-2-thione hydrochloride | Compound 16 |
| 19 | (R)-5-(2-aminoethyl)-1-(8-hydroxychroman-3-yl)-1,3-dihydroimidazole-2-thione hydrochloride | Compound 21 |

TABLE 3-continued

| Ex. | Compound | Ref to Table 1 |
|---|---|---|
| 20 | (R)-5-(2-aminoethyl)-1-(6-methoxychroman-3-yl)-1,3-dihydroimidazole-2-thione hydrochloride | Compound 23 |
| 21 | (R)-5-(2-aminoethyl)-1-(8-methoxychroman-3-yl)-1,3-dihydroimidazole-2-thione hydrochloride | Compound 19 |
| 22 | (R)-5-(2-aminoethyl)-1-(6-fluorochroman-3-yl)-1,3-dihydroimidazole-2-thione hydrochloride | Compound 7 |
| 23 | (R)-5-(2-aminoethyl)-1-(8-fluorochroman-3-yl)-1,3-dihydroimidazole-2-thione hydrochloride | Compound 6 |
| 24 | (R)-5-(2-aminoethyl)-1-(6,7-difluorochroman-3-yl)-1,3-dihydroimidazole-2-thione hydrochloride | Compound 8 |
| 25 | (S)-5-(2-aminoethyl)-1-(6,8-difluorochroman-3-yl)-1,3-dihydroimidazole-2-thione hydrochloride | Compound 9 |
| 26 | (R)-5-(2-aminoethyl)-1-(6,7,8-trifluorochroman-3-yl)-1,3-dihydroimidazole-2-thione hydrochloride | Compound 10 |
| 27 | (R)-5-(2-aminoethyl)-1-(6-chloro-8-methoxychroman-3-yl)-1,3-dihydroimidazole-2-thione hydrochloride | Compound 11 |
| 28 | (R)-5-(2-aminoethyl)-1-(6-methoxy-8-chlorochroman-3-yl)-1,3-dihydroimidazole-2-thione hydrochloride | Compound 13 |
| 29 | (R)-5-(2-aminoethyl)-1-(6-nitrochroman-3-yl)-1,3-dihydroimidazole-2-thione hydrochloride | Compound 18 |
| 30 | (R)-5-(2-aminoethyl)-1-(8-nitrochroman-3-yl)-1,3-dihydroimidazole-2-thione hydrochloride | Compound 17 |
| 31 | (R)-5-(2-aminoethyl)-1-[6-(acetylamino)chroman-3-yl]-1,3-dihydroimidazole-2-thione hydrochloride | Compound 14 |
| 32 | (R)-5-(2-aminoethyl)-1-(6-hydroxy-7-benzylchroman-3-yl)-1,3-dihydroimidazole-2-thione hydrochloride | Compound 15 |
| 33 | (R)-5-(2-Benzylaminoethyl)-1-(6-methoxychroman-3-yl)-1,3-dihydroimidazole-2-thione hydrochloride | Compound 25 |
| 34 | (R)-5-(2-Benzylaminoethyl)-1-(6-hydroxychroman-3-yl)-1,3-dihydroimidazole-2-thione hydrochloride | Compound 26 |
| 35 | (R)-1-(6-Hydroxychroman-3-yl)-5-(2-methylaminoethyl)-1,3-dihydroimidazole-2-thione hydrochloride | Compound 27 |
| 36 | (R)-1-(6,8-Difluorochroman-3-yl)-5-(2-methylaminoethyl)-1,3-dihydroimidazole-2-thione hydrochloride | Compound 28 |
| 37 | (R)-1-Chroman-3-yl-5-(2-methylaminoethyl)-1,3-dihydroimidazole-2-thione hydrochloride | Compound 29 |

EXAMPLE 38

(R,S)-5-(2-aminoethyl)-1-(6-methoxythiochroman-3-yl)-1,3-droimidazole-2-thione hydrochloride (compound 30, table 1)

A stirred mixture of 6-methoxythiochroman-3-ylamine hydrochloride (0.12 g, 0.50 mmol), [3-(tert-butyldimethylsilanyloxy)-2-oxopropyl]carbamic acid tert-butyl ester (0.17 g, 0.55 mmol), potassium thiocyanate (0.055 g, 0.55 mmol), water (0.009 g, 0.50 mmol) and acetic acid (0.2 mL, 3.3 mmol) in ethyl acetate (2 mL) was refluxed for 7 hours, cooled to room temperature, washed by sodium bicarbonate solution, dried over anhydrous magnesium sulphate and evaporated in vacuo. The residue was purified by column chromatography on silica using ethyl acetate—petroleum ether mixture as eluent. The resulting oil (0.12 g) was dissolved in ethyl acetate (1 ml), 2M HCl solution in ethyl acetate was added (1 mL, 2 mmol) and the mixture was stirred for 2 hours at room temperature. The precipitate was removed by filtration and washed with ethyl acetate to give crystals which decomposed without melting.

EXAMPLE 39

By the application of the above described technique and related procedures known to those skilled in the art and using the appropriate chroman-3-ylamine hydrochlorides, the following compounds were prepared:

(R,S)-5-(2-aminoethyl)-1-(6-hydroxythiochroman-3-yl)-1,3-dihydroimidazole-2-thione hydrochloride (compound 31, table 1)

EXAMPLE 40

2-[3-(2,2-Dimethyl[1,3]dioxolan-4-yl)propyl]isoindole-1,3-dione

To a stirred solution of 3-(2,2-dimethyl-[1,3]dioxolan-4-yl)propylamine (1.05 g, 6.60 mmol) and carboethoxyphthalimide (1.45 g, 6.60 mmol) in acetonitrile (10 mL) at room temperature was added triethylamine (0.92 mL, 6.60 mmol) in one portion and the resuting mixture was stirred at room temperature for 18 hours, evaporated in vacuo and the residue was dissolved in ethyl acetate (50 mL). The solution was washed with brine, 10% citric acid solution and brine, then dried over anhydrous magnesium sulfate. Filtration and concentration in vacuo gave an oil which was purified by column chromatography on silica using ethyl acetate—petroleum ether mixture as eluent to afford a colourless oil.

EXAMPLE 41

2-(4,5-Dihydroxypentyl)isoindole-1,3-dione

To a stirred solution of 2-[3-(2,2-dimethyl[1,3]dioxolan-4-yl)propyl]isoindole-1,3-dione (1.65 g, 5.70 mmol) in THF (20 mL) at room temperature was added 2N HCl solution (15 mL, 30 mmol) in one portion and the resulting mixture was stirred at room temperature for two hours and then evaporated in vacuo to half of the initial volume. The residue was saturated with NaCl and extracted with ethyl acetate. The organic phase was dried by anhydrous magnesium sulfate. Filtration and concentration in vacuo afforded a colourless oil.

EXAMPLE 42

By the application of the technique described in example 8 to 2-(4,5-dihydroxypentyl)isoindole-1,3-dione, the following compound was prepared:
2-[5-(tert-Butyldimethylsilanyloxy)-4-hydroxypentyl]isoindole-1,3-dione

EXAMPLE 43

By the application of the technique described in example 11 to 2-[5-(tert-butyldimethylsilanyloxy)-4-hydroxypentyl]isoindole-1,3-dione, the following compound was prepared:
2-[5-(tert-Butyldimethylsilanyloxy)-4-oxopentyl]isoindole-1,3-dione

EXAMPLE 44

(S)-5-(3-aminopropyl)-1-(5,7-difluoro-1,2,3,4-tetrahydronaphthalen-2-yl)-1,3-dihydroimidazole-2-thione hydrochloride (compound 5, table 1)

A stirred mixture of (S)-5,7-difluoro-1,2,3,4-tetrahydronaphthalen-2-yl amine hydrochloride (0.22 g, 1.0 mmol), 2-[5-(tert-butyldimethylsilanyloxy)-4-oxopentyl]isoindole-1, 3-dione (0.38 g, 1.05 mmol), potassium thiocyanate (0.11 g, 1.10 mmol), water (0.18 g, 1.0 mmol) and acetic acid (0.3 mL, 5.0 mmol) in ethyl acetate (3 mL) was refluxed for 7 hours, cooled to room temperature, washed by sodium bicarbonate solution, dried over anhydrous magnesium sulphate and evaporated in vacuo. The residue was purified by column chromatography on silica using ethyl acetate—petroleum ether mixture as eluent. The resulting oil (0.18 g) was dissolved in a mixture of isopropanol (5 mL) and THF (2 mL). Water (0.8 mL) and sodium borohydride (0.066 g, 1.74 mmol) were added at room temperature and the mixture was stirred for 1.5 hours. Acetic acid (0.6 ml, 10 mmol) was added and the solution was refluxed for two hours then evaporated in vacuo to dryness. The residue was taken up into acetone, the solid was filtered off, and the filtrate was acidified with 2N HCl solution in ethyl acetate. The precipitate was collected and washed with acetone to afford crystals, which decomposed without melting.

EXAMPLE 45

(R)-5-(3-aminopropyl)-1-(6,8-difluorochroman-3-yl)-1,3-dihydroimidazole-2-thione hydrochloride A stirred mixture of (R)-6,8-difluorochroman-3-ylamine hydrochloride (0.11 g, 0.50 mmol), 2-[5-(tert-Butyldimethylsilanyloxy)-4-oxopentyl]isoindole-1,3-dione (0.19 g, 0.55 mmol), potassium thiocyanate (0.055 g, 0.55 mmol), water (0.009 g, 0.50 mmol) and acetic acid (0.15 mL, 2.5 mmol) in ethyl acetate (1.5 mL) was refluxed for 7 hours, cooled to the room temperature, washed by sodium bicarbonate solution, dried over anhydrous magnesium sulphate and evaporated in vacuo. The residue was purified by column chromatography on silica using ethyl acetate—petroleum ether mixture as eluent. The resulting oil (0.10 g) was dissolved in the mixture of isopropanol (2.5 mL) and THF (1 mL). Water (0.4 mL) and sodium borohydride (0.038 g, 1.0 mmol) were added at room temperature and the mixture was stirred for 1.5 hours. Acetic acid (0.3 ml, 5 mmoj) was added and the solution was refluxed for two hours and evaporated in vacuo to dryness. The residue was taken up in acetone, the solid was filtered off, and the filtrate was acidified with 2N HCl solution in ethyl acetate. The precipitate was collected and washed with acetone to afford crystals, which decomposed without melting.

EXAMPLE 46

(R,S)-5-(3-aminopropyl)-1-(6-hydroxythiochroman-3-yl)-1,3-dihydroimidazole-2-thione hydrochloride A stirred mixture of 6-hydroxythiochroman-3-ylamine hydrochloride (0.22 g, 1.0 mmol), 2-[5-(tert-Butyldimethylsilanyloxy)-4-oxopentyl]isoindole-1,3-dione (0.38 g, 1.05 mmol), potassium thiocyanate (0.11 g, 1.10 mmol), water (0.18 g, 1.0 mmol) and acetic acid (0.3 mL, 5.0 mmol) in ethyl acetate (3 mL) was refluxed for 7 hours, cooled to room temperature, washed by sodium bicarbonate solution, dried over anhydrous magnesium sulphate and evaporated in vacuo. The residue was purified by column chromatography on silica using ethyl acetate—petroleum ether mixture as eluent. The resulting oil (0.17 g) was dissolved in the mixture of isopropanol (5 mL) and THF (2 mL). Water (0.8 mL) and sodium borohydride (0.066 g, 1.74 mmol) were added at room temperature and the mixture was stirred for 1.5 hours. Acetic acid (0.6 ml, 10 mmoj) was added and the solution was refluxed for two hours and evaporated in vacuo to dryness. The residue was taken up into acetone, the solid was filtered off and the filtrate was acidified with 2N HCl solution in ethyl acetate. The precipitate was collected and washed with acetone to afford crystals, which decomposed without melting.

What is claimed is:

1. A compound of Formula III where n signifies 2, $R_4$ signifies hydrogen, an alkyl group or an alkylaryl group; $R_5$ signifies a hydroxyl protecting group and $R_6$ signifies an amino protecting group, wherein the hydroxyl protecting group is an organosilyl group; and the amino protecting group is an alkyl carbamate group or alkylaryl carbamate group, and wherein the term alkyl means a hydrocarbon chain, straight or branched, containing from one to six carbon atoms, optionally substituted by one or more aryl groups, alkoxy groups, halogens, alkoxycarbonyl groups or hydroxycarbonyl groups; the term aryl means a phenyl or naphthyl group, optionally substituted by an alkyloxy group, halogen or nitro group; and the term halogen means fluorine, chlorine, bromine or iodine.

2. A compound of Formula III where n signifies 3, $R_5$ signifies a hydroxyl protecting group; and $R_4$ and $R_6$ taken together represent a phthalimido group, wherein the hydroxyl protecting group is an organosilyl group.

3. A compound of Formula II wherein $R_1$, $R_2$ and $R_3$ may be the same or different and signify fluorine or hydrogen, with the proviso that at least one of $R_1$, $R_2$ and $R_3$ signfies fluorine; and where X signifies an oxygen atom or a sulphur atom.

4. A compound according to claim 3, wherein X signifies an oxygen atom.

5. (R)-6,8-difluoro-3,4-dihydro-2H-1-benzopyran-3-amine.

6. A compound according to claim 1, wherein the compound is [4-(tert-butyldimethylsilanyloxy)-3-oxobutyl]methylcarbamic acid tert-butyl ester.

7. A compound according to claim 1, wherein the compound is [4-(tert-butyldimethylsilanyloxy)-3-oxobutyl]benzylcarbamic acid tert-butyl ester.

8. A compound according to claim 2, wherein the compound is 2-[5-(tert-Butyldimethylsilanyloxy)-4-oxopentyl]isoindole-1,3-dione.

9. A compound according to claim 1 wherein the organosilyl group is a trialkysilyl group, triphenylsilyl group, phenyldialkylsilyl group, tert-butyldimethylsilyl group or an alkyldiphenylsilyl group.

10. A compound according to claim 2 wherein the organosilyl group is a trialkysilyl group, triphenylsilyl group, phenyldialkylsilyl group, tert-butyldimethylsilyl group or an alkyidiphenylsilyl group.

11. A compound according to claim 1 wherein the amino protecting group $R_6$ is a t-butyl carbamate group.

12. A compound according to claim 2 wherein the amino protecting group $R_6$ is a t-butyl carbamate group.

* * * * *